United States Patent
Trad

(10) Patent No.: US 10,932,719 B2
(45) Date of Patent: Mar. 2, 2021

(54) IN-VIVO FLUID MONITORING DEVICES AND METHODS

(71) Applicant: Jawad Trad, Tulsa, OK (US)

(72) Inventor: Jawad Trad, Tulsa, OK (US)

( * ) Notice: Subject to any disclaimer, the term of this patent is extended or adjusted under 35 U.S.C. 154(b) by 0 days.

(21) Appl. No.: 16/896,586

(22) Filed: Jun. 9, 2020

(65) Prior Publication Data

US 2020/0390390 A1 Dec. 17, 2020

Related U.S. Application Data

(60) Provisional application No. 62/921,391, filed on Jun. 14, 2019.

(51) Int. Cl.
*A61B 5/00* (2006.01)
*A61B 5/0533* (2021.01)

(52) U.S. Cl.
CPC .......... *A61B 5/4875* (2013.01); *A61B 5/0022* (2013.01); *A61B 5/0533* (2013.01); *A61B 5/6807* (2013.01); *A61B 5/742* (2013.01); *A61B 5/746* (2013.01); *A61B 5/7465* (2013.01)

(58) Field of Classification Search
CPC ... A61B 5/0022; A61B 5/0533; A61B 5/4875; A61B 5/6807; A61B 5/742; A61B 5/746; A61B 5/7465
See application file for complete search history.

(56) References Cited

U.S. PATENT DOCUMENTS

| | | | |
|---|---|---|---|
| 3,534,727 A | 10/1970 | Roman | |
| 3,870,034 A | 3/1975 | James | |
| 5,546,955 A | 8/1996 | Wilk | |
| 6,216,545 B1 | 4/2001 | Taylor | |
| 6,381,482 B1 | 4/2002 | Jayaraman | |
| 6,729,025 B2 | 5/2004 | Farrell | |
| 6,970,731 B1 | 11/2005 | Jayaraman | |
| 7,308,294 B2 | 12/2007 | Hassonjee | |
| 8,140,143 B2 | 3/2012 | Picard | |
| 8,214,007 B2 | 7/2012 | Baker | |
| 8,925,392 B2 | 1/2015 | Esposito | |
| 9,186,092 B2 | 11/2015 | Mestrovic | |
| 9,247,907 B2 | 2/2016 | Oleson | |
| 9,662,053 B2 | 5/2017 | Richards | |
| 9,817,959 B2 | 11/2017 | Dadu | |

(Continued)

OTHER PUBLICATIONS

R. Picard et al., The Galvactivator: A Glove that Senses and Communicates Skin Conductivity, Proc. of 9th International Conference on Human-Computer Interaction, pp. 1538-1542 (2001).

(Continued)

*Primary Examiner* — Max F Hindenburg

(74) *Attorney, Agent, or Firm* — John M. Behles

(57) ABSTRACT

In-vivo fluid monitoring devices and methods are disclosed herein. An example device is configured for patients which monitors increases and decreases of fluid retention in patients with various clinical conditions such as heart and renal failure pre-operation and post operation thus allowing physicians to more accurately detect said fluid retention gains through a mechanism directly or indirectly connected to circulatory stocking which act as a conduit to detect said fluid changes through skin electrolysis and alterations respective to fluid changes directly corresponding with galvanic skin response measurement changes.

20 Claims, 14 Drawing Sheets

(56) References Cited

U.S. PATENT DOCUMENTS

| | | | |
|---|---|---|---|
| 9,913,611 B2 | 3/2018 | Wiebe | |
| 9,955,916 B2* | 5/2018 | Bonomi | A61B 5/6823 |
| 9,999,352 B2 | 6/2018 | Enrico | |
| 10,105,108 B1 | 10/2018 | Taptelis | |
| 10,607,507 B2* | 3/2020 | Connor | A61B 5/6826 |
| 2015/0297100 A1 | 10/2015 | Castillo | |
| 2016/0066840 A1* | 3/2016 | Russell | A61B 5/1116 |
| | | | 600/301 |
| 2016/0174898 A1* | 6/2016 | Udoh | A61B 5/02055 |
| | | | 600/301 |
| 2017/0079868 A1* | 3/2017 | Reid, Jr. | A61B 5/0053 |
| 2017/0319132 A1* | 11/2017 | Longinotti-Buitoni | |
| | | | A61B 5/0205 |
| 2018/0140237 A1* | 5/2018 | Rajan | A61B 5/02438 |

OTHER PUBLICATIONS

T. Westeyn et. al, ActionGSR: A Combination Galvanic Skin Response-Accelerometer for Physiological Measurements in Active Environments, iscw, pp. 129-130, 2006 10th IEEE Internaitional Symposium on Wearable Computers, 2006.

A Galvanic Intrabody Method for Assessing Fluid Flow in Unilateral Lymphoedema; Electronics Published: Jun. 15, 2017, CO ASOGWA.

Sensing Fabrics for Monitoring Physiological and Biomechanical Variables: Etextile solutions; PACELLI.

Performance Evaluation of Sensing Fabrics for Monitoring Physiological and ;Biomechanical Variables, IEEE Transactions on Information Technology in Biomedicine, vol. 9, No. 3, Sep. 2005, Enzo Pasquale Scilingo.

* cited by examiner

IN-VIVO FLUID MONITORING DEVICES AND METHODS

CROSS-REFERENCE TO RELATED APPLICATION(S)

This non-provisional application claims the benefit and priority of U.S. provisional application Ser. No. 62/921,391, titled "Methods of In Vivo Fluid Monitoring with Compression Stocking Attachments", filed on Jun. 14, 2019, which is hereby incorporated by reference herein in its entirety, including all references and appendices cited therein, for all purposes, as if fully set forth herein.

TECHNICAL FIELD

The present disclosure relates to fluid monitoring in patients, and more particularly, but not by way of limitation, to systems and methods for in-vivo fluid retention and detection of patients to monitor increases and decreases of fluid retention in patients with various clinical conditions such as heart and renal failure pre-operation and post operation.

SUMMARY

An example embodiment of a device includes a compression stocking; a first lead integrated into the compression stocking; a second lead integrated into the compression stocking, wherein a terminal end of the first lead and a terminal end of the second lead are spaced apart from one another, each of the terminal ends being capable of contacting skin of a foot of a patient; and a control unit configured to electrically couple with the first lead and the second lead, the control unit comprising a microcontroller configured to measure galvanic skin response values of the patient over time, the galvanic skin response values being indicative of a fluidic retention of the patient.

In some embodiments, the microcontroller is configured to convert the galvanic skin response values to fluidic volume values. The first lead comprises a first conductive interface disposed at a top of the compression stocking and the second lead comprises a second conductive interface disposed at the top of the compression stocking.

In some embodiments, the control unit comprises a first conductor pin and a second conductor pin, the first conductor pin being configured to snap into the first conductive interface, the second conductor pin being configured to snap into the second conductive interface, the first conductor pin and the second conductor pin being electrically coupled to the microcontroller. The galvanic skin response values are obtained according to a user-defined interval.

In some embodiments, the control unit comprises a communications module that allows for transmission of the galvanic skin response values or fluidic volume values to a service provider over a network.

In some embodiments, the microcontroller is configured to store a fluid volume threshold, further wherein when the fluidic retention of the patient meets or exceeds the fluid volume threshold, the microcontroller transmits an alert message to over the network to a service provider.

In some embodiments, the first lead functions as an anode and the second lead functions as a cathode.

An example device can include a garment that is worn on a patient, the garment comprising a anode lead and a cathode lead woven into the garment; and a control unit configured to electrically couple with the anode lead and the cathode lead, the control unit being configured to: emit transmitted electrical signals through the anode lead; measure received electrical signals from the cathode lead; calculate galvanic skin response based on the transmitted electrical signals and the received electrical signals; and convert the galvanic skin response to fluid volume.

In some embodiments, the the control unit collects the galvanic skin response over a period of time to determine changes in the fluid volume over the period of time. In some embodiments, the control unit is configured to transmit an alert to a physician when the fluid volume exceeds a fluid volume threshold or trigger.

In some embodiments, the anode lead comprises a first conductive interface and the cathode lead comprises a second conductive interface. In some embodiments, the control unit comprises a housing that encloses a microcontroller, a resistive-capacitive time circuit, and a communications interface.

In some embodiments, the housing comprises a first conductor pin and a second conductor pin, the first conductor pin being configured to snap into the first conductive interface, the second conductor pin being configured to snap into the second conductive interface, the first conductor pin and the second conductor pin being electrically coupled to the microcontroller. In some embodiments, the galvanic skin response values are obtained according to a user-defined interval.

According to some embodiments, a method includes providing a compression stocking to a patient, the compression stocking comprising a first lead integrated into the compression stocking and a second lead integrated into the compression stocking, the compression stocking comprising a control unit that is configured to generate galvanic skin response data or fluid volume data; and transmitting the galvanic skin response data or the fluid volume data from the control unit to a service provider.

In some embodiments, the method includes generating a graphical display of the galvanic skin response data or the fluid volume data. In some embodiments, the method includes obtaining a baseline fluid volume for the patient. In some embodiments, the method includes determining when the fluid volume data meet or exceed a threshold compared with the baseline fluid volume; and transmitting an alert to a physician when the fluid volume data meet or exceed the threshold. In some embodiments, the method includes converting, by the service provider, the galvanic skin response data into the fluid volume data.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
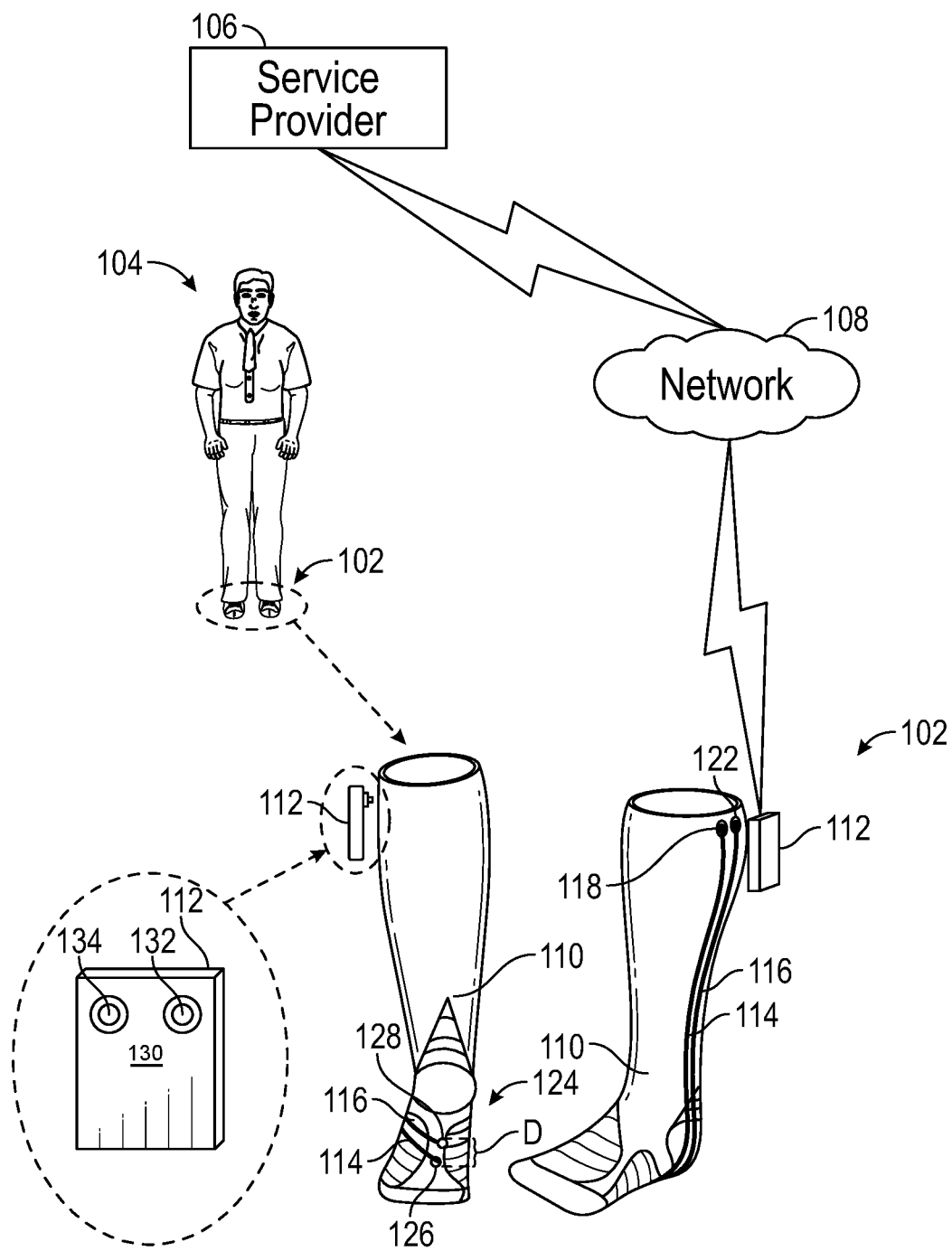
FIG. 1 depicts an illustrative architecture in which techniques and structures for providing the systems and methods disclosed herein may be implemented.

There are various medical conditions causing inappropriate fluid volume overload in patients producing symptoms of shortness of breath, swelling of lower extremities or central bodily retention leading to pain, decreased appetite, bloating among other symptoms.

The devices, systems, and methods disclosed herein detect volume overload caused by disease processes such as heart failure. Example devices as disclosed herein allow physicians to more accurately detect fluid retention gains through a mechanism directly or indirectly connected to circulatory stocking which act as a conduit to detect fluid changes through skin electrolysis and alterations respective to fluid changes directly corresponding with galvanic skin response (GSR) measurement changes.

Every year in the United States, more than 650,000 individuals are newly diagnosed with heart failure (HF) and the lifetime risk of developing this syndrome is one in five. Heart failure is one of the largest clinical challenges facing healthcare today, affecting nearly six million Americans and accounting for 1.2 million hospitalizations every year. The current U.S. expenditures for heart failure exceed $30 billion annually, with 60-80 percent related to hospitalization, and these figures are expected to grow in the future. Prevalence is expected to nearly double by the year 2030.

Chronic heart failure reduces quality and quantity of life and is expensive for healthcare systems. Medical treatment relies on guideline-directed therapy, but clinical follow-up and remote management is highly variable and poorly effective. Management strategies are needed to maintain clinical stability and avoid hospitalizations for acute decompensation. Chronic HF is a clinical syndrome characterized by the heart's inability to provide adequate flow to meet the body's needs, particularly on exertion. This syndrome arises from myocardial dysfunction resulting in a mixture of decreased contractility during systole (HF with reduced ejection fraction, HFrEF) or an inability to appropriately fill the ventricles during diastole (HF with preserved ejection fraction, HFpEF) with resultant neurohormonal activation. Elevated pulmonary artery (PA) pressures are common features of both HFrEF and HFpEF and are associated with the subsequent increased risk for mortality5 or decompensation requiring hospitalization.

A high percentage of patients experience rapidly recurring symptoms requiring re-hospitalization shortly after discharge. Several clinical management strategies designed to closely monitor for evidence of accumulating volume or early detection of symptoms have been tested with the goal of reducing the need for hospitalization, by acting on changes in a remotely monitored signal, such as daily weight measurements, patient reported symptoms, B-type natriuretic peptide levels, or non-hemodynamic physiologic signals derived from implanted devices, such as intrathoracic impedance. Unfortunately, most studies failed to reduce the need for HF hospitalizations, but a minority has suggested the potential for an improvement in survival in closely monitored patients.

Most physicians desire to monitor a patient's fluid retention. To date there are devices, most of which are invasive, however none addressing the real-time monitoring of fluid retention changes over prolonged time. A cardiologist who performs surgery on a patient needs to see said patient's fluid retention in real time to make better determinations on how to adjust the patient's diuretics. Diuretics cause a host to decrease fluid retentions.

Lymphedema is a disease associated with swelling of the body due to accumulation of tissue fluid in affected area. The tissue fluid contains ions and electrolytes that affect electrical conductivity. The flow of tissue fluid helps to distribute vital nutrients and other important elements necessary for a healthy host. When tissue fluid is stagnated, a high concentration of electrolytes accumulate in the affected area, which in turn affects an electrical signal passing through that area to be minimally attenuated in relation to a free-flowing fluid. In this application we will assert the galvanic coupled signal propagating along a lymphedema affected limb captures these changes by the amount of attenuation the propagating signal experiences in time. These results shown in vivo studies that average rate of signal attenuation on a lymphedema affected part of the body could be as slow as 0.16 dB/min (Decibels per minute), while the rate of signal attenuation on a healthy part is as high as 1.83 dB/min. This means that fluid accumulation could slow down the exchange of body electrolytes up to twice less the rate on an unaffected contralateral part of the body or in relation to a previously documented euvolemic state.

Monitoring these changes by observing the average rate of change of galvanic coupled signal attenuation on the affected body part can be used for diagnosing early developments of lymphedema in the body and for evaluating recovery in response to treatment procedures. Congestion, otherwise known as "fluid overload", is a common clinical symptom of patients who have heart failure and its presence is associated with an adverse outcome. Congestion is not always clinically evident, and more objective measures of congestion than simple clinical examination may assist a physician in proper diagnosis. Although diuretics are mainly used as a treatment for congestion, there are no randomized trials that have logged the effects of diuretics on mortality in chronic heart failure patients. It's also noted an appropriate titration of diuretics in this population of patients is unclear. A need therefore exist to determine whether a robust method of detecting fluid retention and then treating subclinical congestion or the root cause of fluid retention or overload will improve the outcomes. Considering that over-diuresing may cause renal impairment, or withholding diuretics prematurely may cause volume overload and symptoms of shortness of breath, among other symptoms makes a strong case for an additional method to determine volume status in such patient population.

Disclosed herein are systems and methods of utilizing compression stockings with intelligent micro-attachments can be used to log and transmit collected patient fluid retention information of lymphatic tissue fluid gains to a mobile device which can be remotely monitored by a remote physician monitoring said patient's fluid retention history.

The present disclosure pertains to devices, systems, and methods of that detect, in real-time or near-real-time, fluid retention and detection in a patient. Increases and/or decreases of fluid retention in patients with various clinical conditions such as heart and renal failure pre-operation and post operation can be measured. Physicians can be enabled to more accurately detect fluid retention gains and losses through a mechanism directly or indirectly connected to an example device which is configured to detect said fluid changes. In some embodiments, the example device detects changes in fluid volume in a patient using skin electrolysis and alterations respective to fluid changes directly corresponding with galvanic skin response measurement changes.

An example device or system as disclosed herein can include any combination of various components. An example device can include a compression stocking with an embedded anode and cathode, a signal generator for producing a known electrical signal stimulant to the embedded anode. The signal is passed through the host dermal surface to the cathode. A signal measurement module senses electrical signal changes of dermal conductivity based on signals entering the anode and exiting the cathode. A processor can be used to convert signal measurements between the anode and cathode electrical stimulant variations. These data and resulting transformations of the data can be stored as digital information. The example device can include a communications module for transmitting logged information periodically to a receiving unit. The receiving unit can be configured to store information obtained from the example device. A virtual platform can be included that generates a visual interface associated with stored information. Some devices can be configured to transmit stored information of a first user to a remote location to be viewed by a second user over a network. Some example devices can be configured to receive first user data at a remote location on a network to be viewed by a second user. Some example devices can be configured to convert received data from a first user to a visual interface viewed by a remote viewer second user over a network.

Example Embodiments

Turning now to the drawings, FIG. 1 depicts an illustrative architecture in which techniques and structures of the present disclosure may be implemented. The architecture includes a fluid monitoring device 102, a patient 104, a service provider 106, and a network 108. The network 108 can include any one or a combination of multiple different types of networks, such as cable networks, the Internet, wireless networks, and other private and/or public networks. In some instances, the network 108 may include cellular, Wi-Fi, or Wi-Fi direct. The network 108 can include any long- or short-range wireless network.

Where appropriate, the functions described herein can be performed in one or more of hardware, software, firmware, digital components, or analog components. For example, the encoding and or decoding systems can be embodied as one or more application specific integrated circuits (ASICs) or microcontrollers that can be programmed to carry out one or more of the systems and procedures described herein. Certain terms are used throughout the description and claims refer to particular system components. As one skilled in the art will appreciate, components may be referred to by different names. This document does not intend to distinguish between components that differ in name, but not function.

The example fluid monitoring device 102 disclosed herein is intended for use in outpatient clinic and home settings and is indicated for patients requiring fluid management. The device 102 is a non-invasive device that is worn by patients 24 hours a day (other periods of time can be utilized). The fluid monitoring device 102 continuously records, stores, and transmits patient data. The fluid monitoring device 102 utilizes a proprietary algorithm to determine patient-specific trends in the data collected by the fluid monitoring device 102, allowing for early detection of heart failure exacerbations therefore preventing further deterioration in the patient's condition. The patient owns the data on their phone and the physician's office may receive notifications when the patient's fluid status is out of range so early non-invasive intervention is ordered by the physician.

The fluid monitoring device 102 may comprise of a galvanic skin response circuit and a microcontroller unit (MCU) which reads the GSR data over time and logs it locally on a mobile device application. A "GSR" comes from the measure of the charge or discharge time of a resistor/capacitor circuit "RCTime" where the skin conductance changes respectively to the patient's fluid retention. This number is between 0-1024.

Example A (Patient A): RCTime signature is normal at 50 and readings of 56, 49, 60, 44, 101, 75, 66, 55, 44, 49, 51 . . . . You notice the progression to a spike to 101 and then a slow decline to normal range. This might signify movement and not necessarily a spike in fluid retention rather fluid loss.

Example B (Patient B): You notice an increase that is gradual and steady, i.e.; 50, 61, 74, 88, 105, 133, 205, 311, 344, 351, 329, 330, 342 . . . . Then this will indicate a fluid retention model.

These numbers can be presented graphically on a mobile device or other computing system. This data may be transmitted to a patient web account where a physician with proper permissions can view said patient's data. You can even set PHP Webmail notification services which are based on triggers or fluid volume threshold values. For example, if the fluid retention score exceeds 500 a message can be transmitted to the physician. After 24 hours of recording every five minutes for the first 24 hours normal or baseline GSR value is set.

Based on the data, the physician can select one or more interventions, or therapies if needed. Therapies used to reduce intravascular volume, such as diuretics, alleviate symptoms and help to maintain clinical stability, allowing patients to resume normal activities outside the hospital.

The fluid monitoring device 102 can include a compression stocking 110, a control unit 112, a first lead 114, and a second lead 116. In some embodiments, the compression stocking 110 is configured to be worn on a leg of the patient 104. In one or more embodiments, the first lead 114 can function as an anode conductive thread that terminates at an upper portion of the compression stocking 110 with a first conductive interface 118. The first lead 114 can be a silver or gold thread, although other similar conductive materials can be used to create the first lead 114. The first conductive interface 118 can include a snap or other similar interface.

The second lead 116 can function as a cathode conductive thread that terminates at an upper portion of the compression stocking 110 with a second conductive interface 122. The second lead 116 can be a silver or gold thread, although other similar conductive materials can be used to create the second lead 116. The second conductive interface 122 can include a snap or other similar interface. To be sure, the assignment of anode to the first lead 112 and the assignment of cathode to the second lead 114 is for descriptive purposes only and these leads can be switched with respect to their use.

In some instances, both the first lead 114 and the second lead 116 can be woven into the fabric of the compression stocking 110 in a zigzag pattern. The first lead 114 terminates on a bottom 124 of the compression stocking 110. In some instances, the first lead 114 has a terminal end 126 that is exposed on a lower inside surface (near or on a gusset area, heel turn, or foot area of the compression stocking 110) of the compression stocking 110 so that when the patient's foot is placed in the compression stocking 110, the bottom of the patient's foot contacts the terminal end 126 of the first lead 114. The terminal end 126 could be formed as a zigzag of the material of the first lead 114, or as a conductive pad, by example.

The second lead 116 also terminates on the bottom 124 of the compression stocking 110. In some instances, the second lead 116 has a terminal end 128 that is exposed on a lower inside surface (near or on a gusset area, heel turn, or foot area of the compression stocking 110) of the compression stocking 110 so that when the patient's foot is placed in the compression stocking 110, the bottom of the patient's foot contacts the terminal end 126 of the second lead 116. The terminal end 128 could be formed as a zigzag of the material of the second lead 116, or as a conductive pad.

To be sure, when the foot is inserted into the compression stocking 110, skin of the patient's foot contacts the terminal end 126 of the first lead 114 and the terminal end 126 of the second lead 116. The bare skin contact allows for transmission of electrical signals from the terminal end 126 of the first lead 114 into the foot of the patient and into the terminal end 126 of the second lead 116. In some embodiments, a conductive gel or compound can be placed between the terminal ends and the skin of the foot to improve conductivity.

While some embodiments contemplate the terminal ends 126 and 128 need not always contact a bottom of the patient's foot, but may be disposed on other portions of the foot. Further, rather than contacting the foot, the terminal ends 126 and 128 may contact the patient's leg. For example, one terminal end may be placed on one side of the leg, while the other terminal end may be placed on an opposing side of the leg.

The terminal end 126 of the first lead 114 and the terminal end 128 of the second lead 116 can be spaced apart from one another at a distance D. The spacing between the terminal end 126 of the first lead 114 and the terminal end 126 of the second lead 116.

The control unit 112 can comprise a housing 130 having a first conductor pin 132 and a second conductor pin 134. The housing 130 is configured to enclose various electrical components, which are schematically illustrated in FIG. 2, and will be discussed in greater detail infra.

Figure 2:
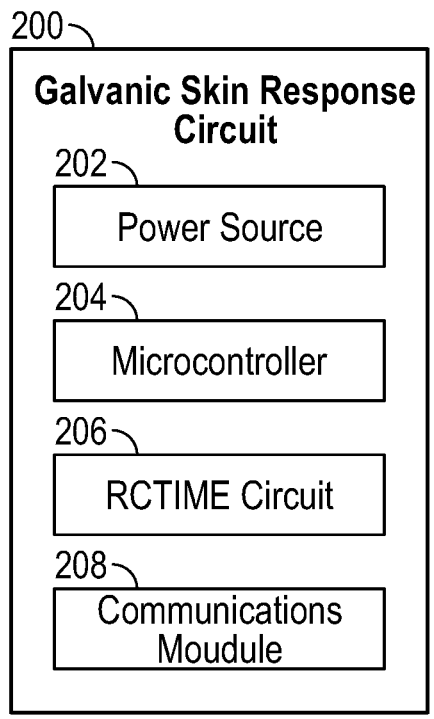
FIG. 2 schematically illustrates an example galvanic skin response circuit.

Referring now to FIGS. 1 and 2 collectively, the first conductor pin 132 is configured to electrically couple or mate with the first conductive interface 118 of the first lead 114. The second conductor pin 134 is configured to electrically couple or mate with the second conductive interface 122 of the second lead 116.

The first conductor pin 132 and the second conductor pin 134 are each respectively coupled to inputs of a galvanic skin response circuit 200. The galvanic skin response circuit 200 can comprise any combination of the components of FIGs. X-X. In one embodiment, the galvanic skin response circuit 200 may comprise a power source 202, a microcontroller 204, and an RCTIME circuit 206. These components may be integrated onto a single PCB (printed circuit board).

In some embodiments, the power source 202 provides electrical current to the RCTIME circuit 206 containing a fixed capacitor one microfarad (1 uf) and a variable resistor to adjust to each patient's electrolyte signal for consistent conductive measurement recordings. In some embodiments, the RCTIME circuit 206 utilizes a time constant which is a measurement of the time needed to charge or discharge its capacitor by ~63.2% of the difference between the old value and new value after an impulse that induces a change has been applied.

The microcontroller 204 calculates an energy (E) and time constant (RC) in a capacitor for the given voltage across the RCTIME circuit 206. Two different values can be determined from the RCTIME circuit 206. Time constant (T) can be determined from the values of capacitance (C) or 1 uf (one microfarad) and load resistance (R) which represents the galvanic skin resistance values (multiple values can be compared to determine a change). Energy stored on a capacitor (E) containing a fixed voltage of five (5) volts can be determined by giving all three inputs: voltage (V), capacitance and load resistance. Since the skin galvanic resistance changes when fluid retention occurs and since the capacitance saturation and voltage is constant, the time constant changes in respect to galvanic skin changes. In general, an energy stored is equal to [voltage $(V)^2$×capacitance (C)]/2; and the time constant is equal to capacitance multiple by load resistance.

It will be understood that GSR values are interpretations of sensor values (sensors being the leads with conductive ends). Using RCTime, the GSR value of skin resistance based on fluid saturation can be determined. The collection of GSR data by the microcontroller 204 utilizes a Bayesian protocol. The microcontroller 204 implements data collection model and constantly feeds input values into the data collection model. The results are amortized to create an arbitration of collected values over time. An example data collection model includes Theta Squared model/time to generate GUI displays.

Load resistance (R) changes can be determined by the microcontroller 204 and corresponding the values recorded with fluid retention. As noted above, the microcontroller 204 comprises firmware to convert RCTime information to a storable value. A real time clock chip (RTC) can be utilized to set the timing of operation and storage synchronizing.

Generally, the galvanic skin response circuit 200 is configured to emit a transmitted electrical signal stimulant to the first conductor pin 132, which is transmitted to the first lead 114 when the control unit 112 is coupled with the compression stocking 110. That is, the first conductor pin 132 is snapped into the first conductive interface 118 of the first lead 114. The second conductor pin 134 is snapped into the second conductive interface 122 of the second lead 116.

The transmitted electrical signal stimulant is transferred through the skin of the patient's foot by the terminal end 126 of the first lead 114 and is received by the terminal end 128 of the second lead 116 as a received electrical signal response. The second lead 116 transfers the received electrical signal response to the second conductor pin 134 and back to the galvanic skin response circuit 200.

The galvanic skin response circuit 200 can be configured to measure a galvanic skin resistive change using both the transmitted electrical signal stimulant and the received electrical signal response. Galvanic skin resistive changes over time are indicative of dermal conductivity changes. The galvanic skin response circuit 200 may operate periodically to obtain various measurements of galvanic skin resistance over time. The galvanic skin response circuit 200 can convert galvanic skin resistance values into a change in fluidic volume for the patient. That is, changes in galvanic skin resistance values are indicative of either an increase or decrease in fluidic volume of the patient.

The galvanic skin response circuit 200 may comprise a communications module 208 for accessing the network 108 of FIG. 1. The communications module 208 may utilize a Diffee and Helman handshaking method where the communications module 208 only operates when requested by the microcontroller 204. Once a request is sent from a master system (such as the service provider 106 of FIG. 1), the communications module 208 can transmit a few bytes to ensure packet integrity. If a full packet is received the handshake is complete and data transfers from a logger of the galvanic skin response circuit 200 to the receiver (such as the service provider 106) where the data is placed in temporary storage for processing.

The communications module 208 may utilize an OFDM platform (Orthogonal Frequency Divisional Multiplexing) protocol which contains an FER or Fractional Error Retry to ensure data packet transfer integrity. If the packet is incomplete, a retry signal is sent back to the transmitter to resend the last data packet sent. Each packet fills a memory address in the receiver which once full is sent for processing to a graphical user interface to be viewed by a remote viewer to interpret the stored information of the RCTime representing the galvanic skin changes due to patient fluid retention.

Data can be transmitted to a remote database in a secured network which can be viewed by a remote viewer who interprets the visual information of the compression stocking fluid retention hosting device. The data may be converted to a CSV (Comma Separated Value) which is then converted to a graphical interface.

In an example use case, when the patient first puts the fluid monitoring device 102 on, a baseline or initial galvanic skin resistance value can be determined. Subsequent measurements of galvanic skin resistance can be obtained at various intervals and differences in galvanic skin resistance values can be determined. Again, these differences are indicative of an increase or decrease in fluidic volume of the patient. In some embodiments, the galvanic skin response circuit 200 can log the galvanic skin resistance values and corresponding fluidic volume values, storing these data locally. In some instances, the galvanic skin response circuit 200 can comprise a communications module 208 that allows the galvanic skin response circuit 200 to transmit the galvanic skin resistance values and/or the corresponding fluidic volume values to the service provider 106, for example. In some embodiments, the galvanic skin response circuit 200 can transfer data synchronously as data are obtained. In other embodiments, the galvanic skin response circuit 200 can batch data and transmit batched data asynchronously.

Also, periodic use of the galvanic skin response circuit 200 to obtain galvanic skin resistance values can also function to save energy during sleep state and wake up and take measurements and go back to a low-current and voltage sleep state. These time intervals can be changed according to user specifications. Some embodiments can allow the galvanic skin response circuit 200 to obtain measurements in a continuous, real-time manner.

The galvanic skin response circuit 200 may comprise a processor and memory for storing executable instructions, such as firmware and/or software. Some example code that may be implemented by the galvanic skin response circuit 200 is set forth below:

```
int sensorPin=4;
//Skin Galvanic Resistance Connected to Anode long
   result=0
void setup( )
//run when the program starts
{
Serial.begin(9600);
}
void loop( )//run over and over again
{
Serial.println(RCtime(sensorPin));
30 delay(10); //timing on/off status can be changed
   according to user
}
long RCtime(int sensPin){long result=0;
pinMode(sensPin, OUTPUT); //make pin OUTPUT
digitalWrite(sensPin, HIGH); //make pin HIGH to dis-
   charge capacitor
delay(1);
//wait a ms to make sure cap is discharged
pinMode(sensPin, INPUT);
//turn pin into an input and time till pin goes low
digitalWrite(sensPin, LOW);
//turn pullups off
while(digitalRead(sensPin)){
//wait for pin to go low result++;
}
return result;
//report results to be stored in the digital medium
```

Figure 3:
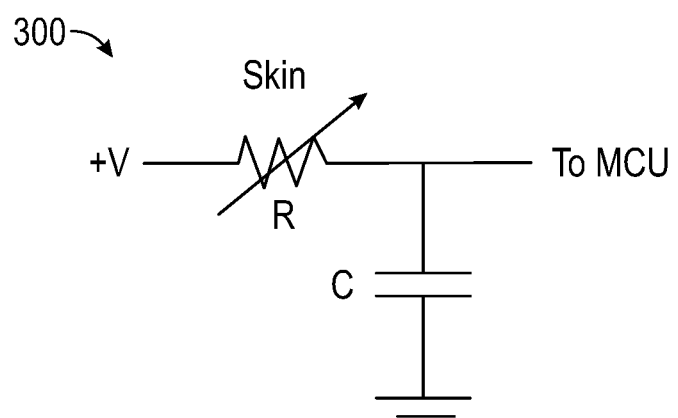
FIG. 3 illustrates a basic RCTIME (resistive-capacitive time) circuit diagram having a fixed capacitor and a variable resistor representing the patient's dermal layer.

FIG. 3 illustrates a basic RCTIME (resistive-capacitive time) circuit diagram 300 having a fixed capacitor C and a variable resistor R representing the patient's dermal layer. An output to an MCU connects to an example microcontroller. When the patient retains or loses fluid, their skin resistance inherently changes proportionally to their fluid retention levels.

Figure 4:
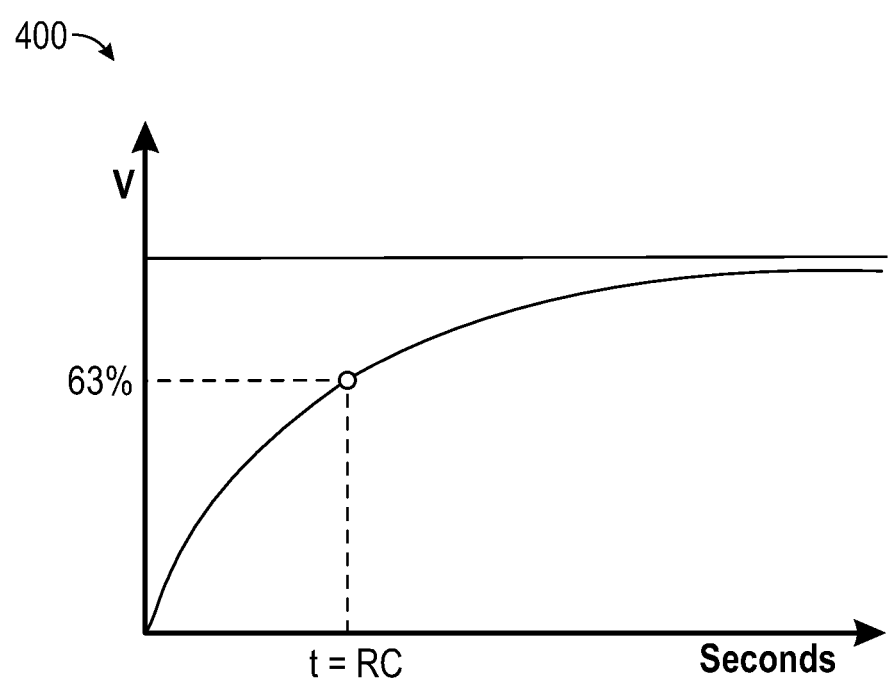
FIG. 4 illustrates an RCTIME curve which illustrates rise and fall of voltage through a capacitor which is regulated by resistance (patient's dermal layer).

FIG. 4 illustrates an RCTIME curve 400 which illustrates rise and fall of voltage through a capacitor which is regulated by resistance (patient's dermal layer). The RC time constant, also called tau, the time constant (in seconds) of an RC circuit, is equal to the product of the circuit resistance (e.g., patient's resistance of dermal layer in ohms) and the circuit fixed known capacitance (in farads).

Figure 5:
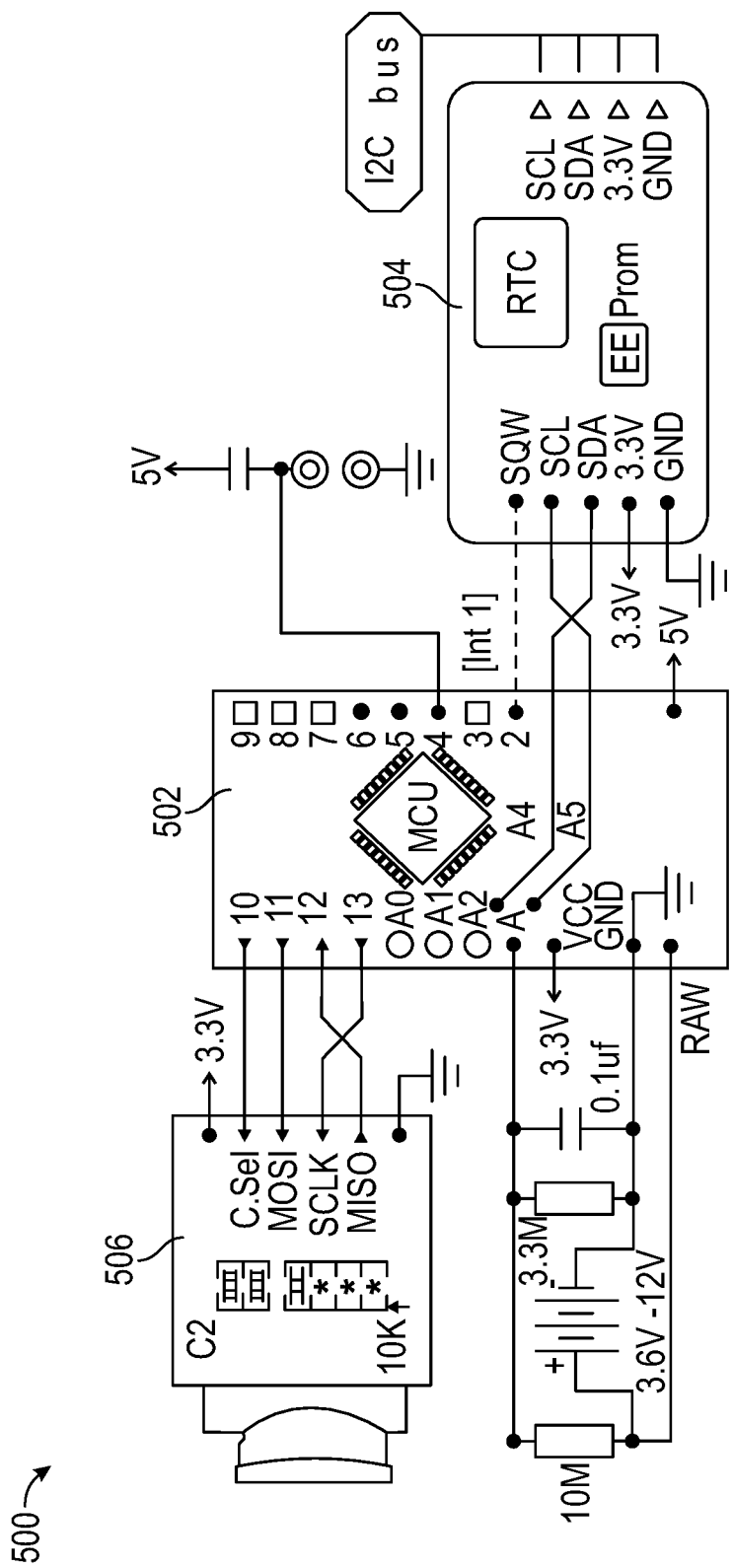
FIG. 5 illustrates a circuit diagram of an example circuit 500 that can be utilized in the present disclosure.

FIG. 5 illustrates a circuit diagram of an example circuit 500 that can be utilized in the present disclosure. The circuit 500 comprises a microcontroller (MCU 502), an RCTIME module 504, and a communications module or serial peripheral interface 506. The circuit 500 can be configured to record a patient's RCTIME representing resistive changes in the patient's dermal layer due to fluid retention. Generally speaking, data loggers are electronic devices which automatically monitor and record environmental parameters over time, allowing conditions to be measured, documented, analyzed and validated. The data logger contains a sensor to receive the data and a computer chip (MCU) to store the data.

The circuit 500 comprises a digital medium used for recording digital information which is stored for future access. This information I/O is controlled by the MCU 502 which records RCTIME that directly corresponds to galvanic skin response (GSR) of the patient. The GSR reading collected by anode and cathode located on the inside of compression stockings (see FIG. 1). A data logger circuit PCB is enclosed in the housing 130 of the control unit 112.

Figure 6:
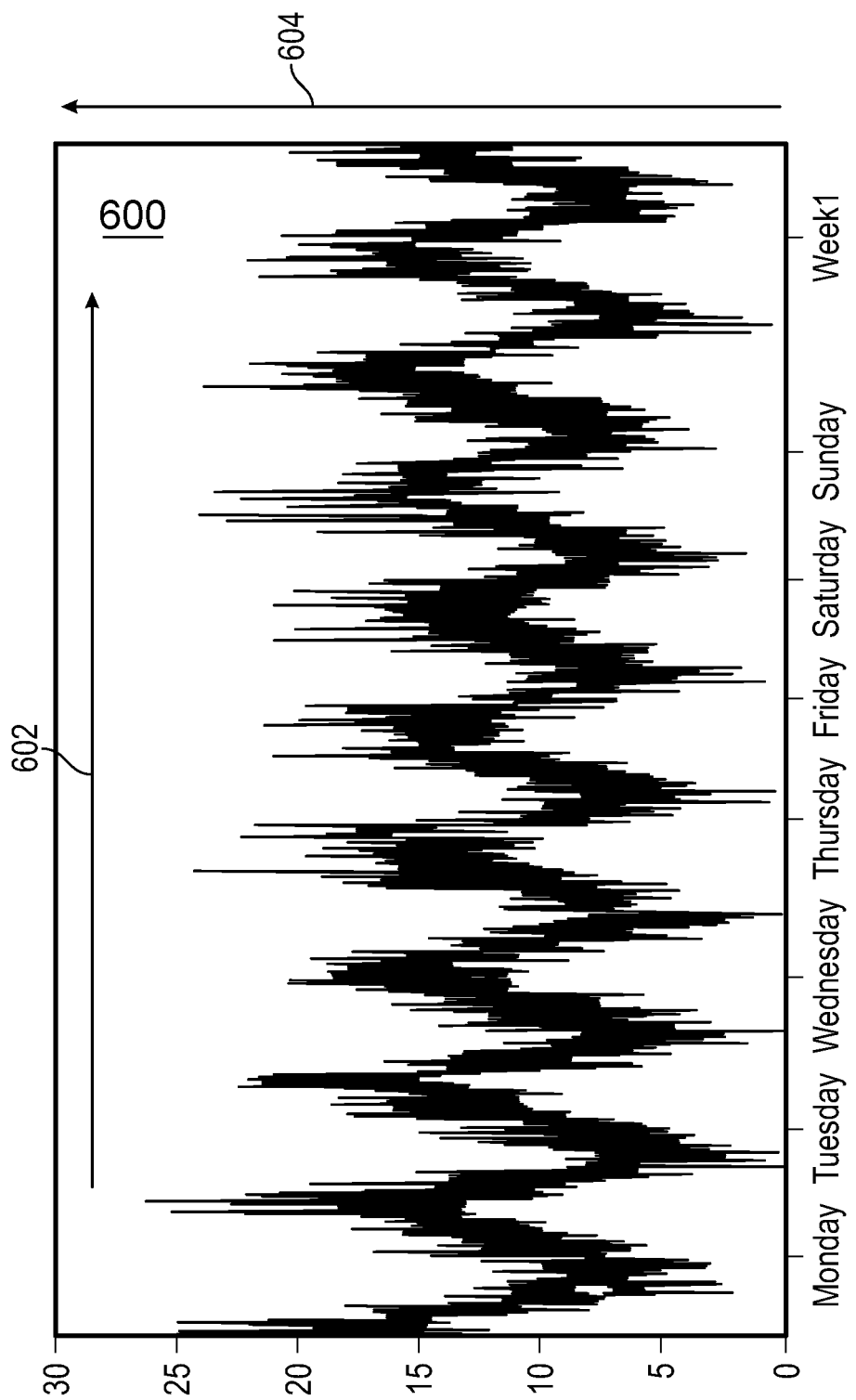
FIG. 6 illustrates an example time graph 600 showing trending data of analog values in the rise and fall of a patient's dermal resistive measurements which demonstrates trending data.

FIG. 6 illustrates an example time graph 600 showing trending data of analog values in the rise and fall of a patient's dermal resistive measurements which demonstrates trending data. A horizontal axis of the graph includes time values 602. These data are correlated to arbitrated amplitude values 604 which are oriented to a vertical axis of the graph. In this application, said GSR collected data in said time graph utilizes values collected over period of use. A given time frame is allocated to first measure average dermal resistance to gain a base line. After time frame allocated has calculated and arbitrated GSR reading values, the graph will then begin to represent time values 602 and amplitude values 604 to represent fluid retention readings of the patient. Data indicative of changes in dermal resistance for a patient can be stored and relayed to a service provider (see 106 of FIG. 1). Collected data can also be transmitted to a mobile device which displays graphics relating to the GSR trending data.

Figure 7:
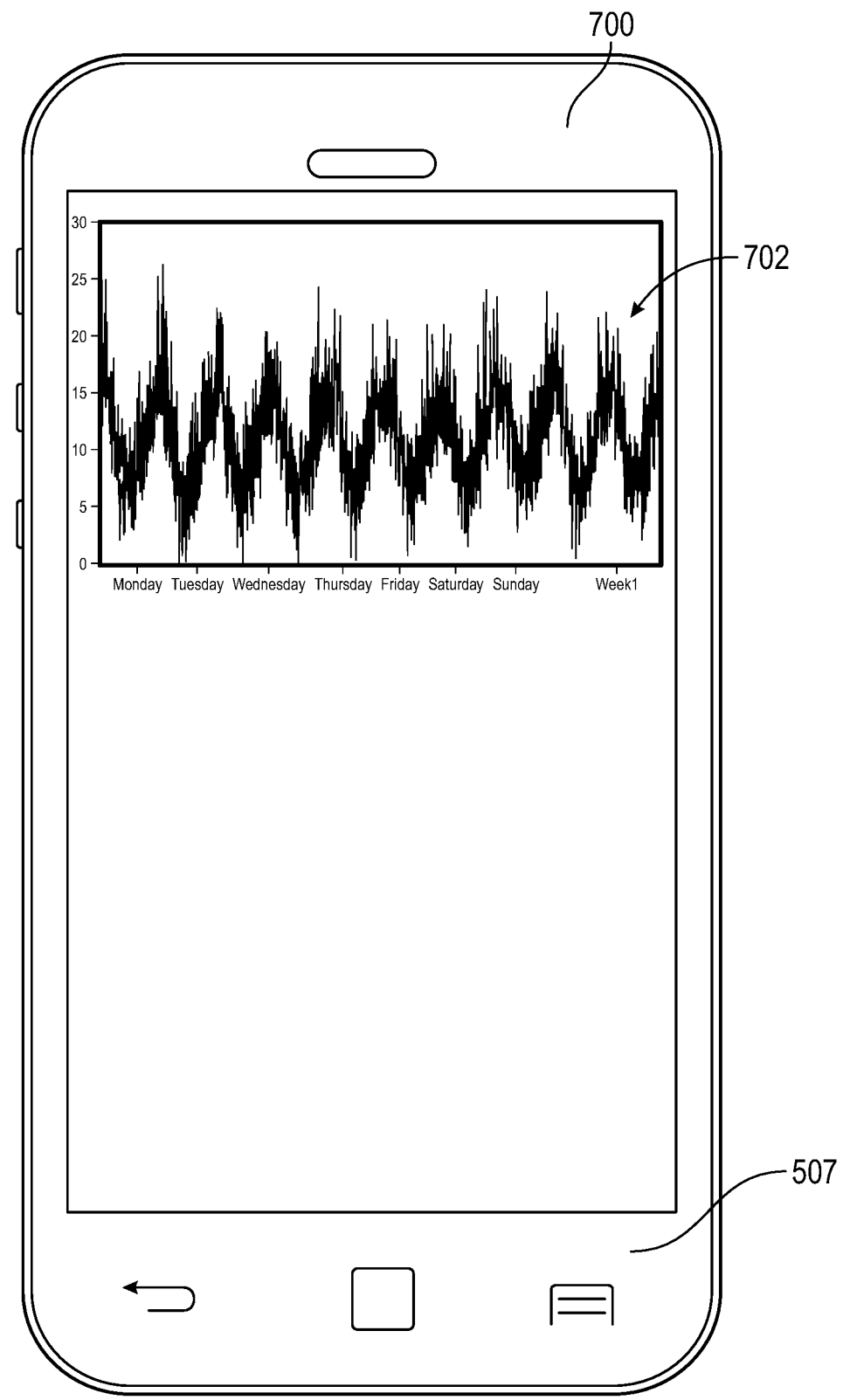
FIG. 7 illustrates an example mobile device that is displaying a user interface that includes trending fluid retention data of a patient.

FIG. 7 illustrates an example mobile device 700 that is displaying a GUI 702 that includes trending fluid retention data of a patient. The mobile device 700 can receive these data from a microcontroller (such as the example microcontroller 204 (see FIG. 2)). A control unit of an example fluidic retention device (see FIGS. 1 and 2) can transmit fluidic volume data to the mobile device 700 for display on the GUI 702.

Figure 8:
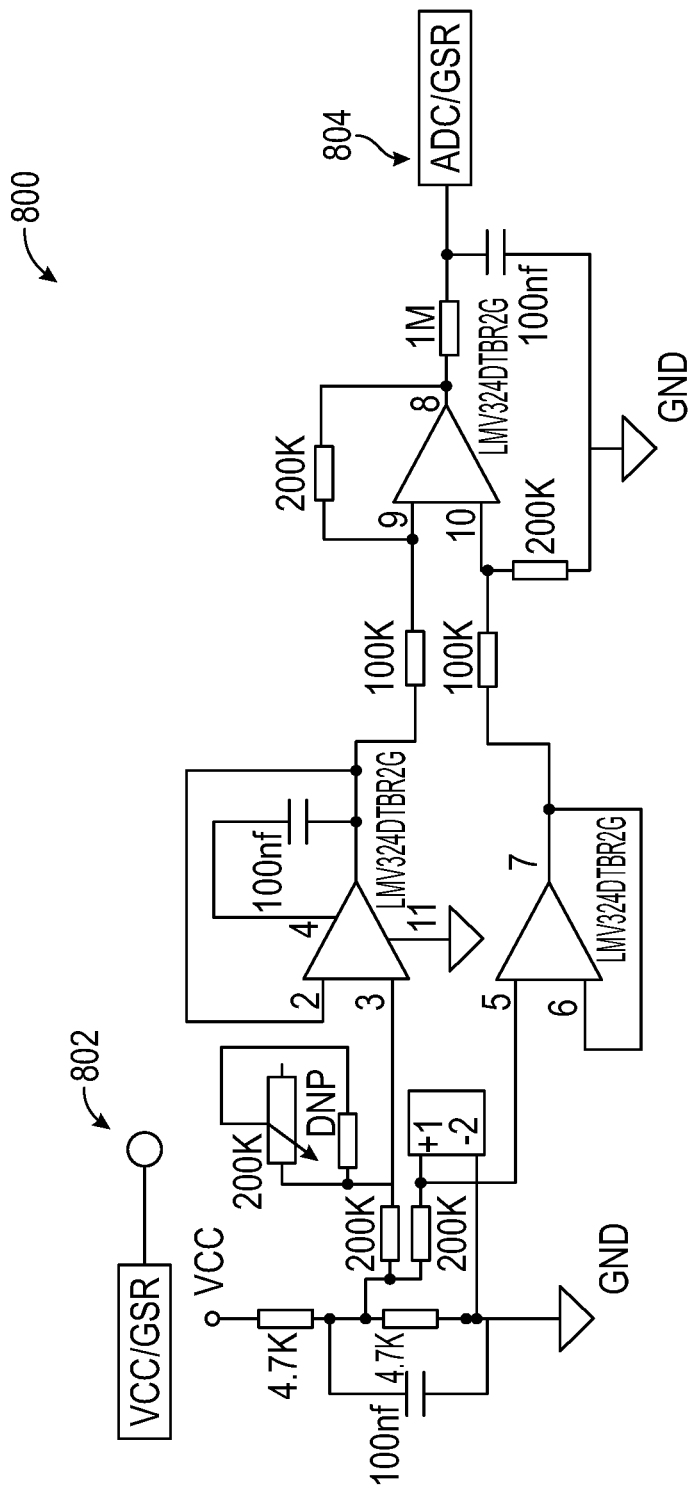
FIG. 8 illustrates a circuit diagram of an example GSR amplifier circuit.

FIG. 8 illustrates a circuit diagram of an example GSR amplifier circuit 800 that can be utilized in the galvanic skin response circuit 200 of FIG. 2. The amplifier circuit 800 comprises at least a GSR sensor electrode; an instrumentation amplifier for GSR signal conditioning; a battery; a charging IC for battery; a ESP32 Microcontroller; a USB connector and USB to UART converter IC; a 3.3V regulator; and a RTC IC and cell.

The GSR electrodes (corresponding to the first and second leads 114 and 116 of FIG. 1, by example) measure conductance from the skin of the patient (e.g., from the bottom of the patient's foot as an example) to the amplifier circuit 800. The amplifier circuit 800 sends the signal to microcontroller ESP32 analog to digital (ADC) pin 10. Microcontroller can read the signal via ADC and after taking the average the microcontroller sends values to a universal asynchronous receiver/transmitter UART or a serial controller interface.

The amplifier operates with voltages as low as 2.7 V and features input and output rail-to-rail, 145 µA consumption current, and 1 (one) MHz gain bandwidth product (GBP). It has a low consumption and a sufficient GBP for the GSR board application.

Pin configurations for the amplifier are shown in each of the two comparators. The input associated with one lead (anode/first lead 114 of FIG. 1) would be VCC/GSR 802 and the input associated with the other lead (cathode/second lead 116 of FIG. 1) would be ADC/GSR 804.

A Human Body Model interface or HBM utilizes a 100 pF capacitor which is charged to the specified voltage, then discharged through a 1.5 kΩ resistor between two pins of the device. These two pins act as an anode and cathode collecting the variation changes in GSR values of the skin when there are fluid retention changes.

The designs herein can be configured for low 3.3V operation rather than 5V circuitry because of size constraints. However, the fundamentals for using RCTime circuit still apply even though the circuit is reading differential information.

Figure 9:
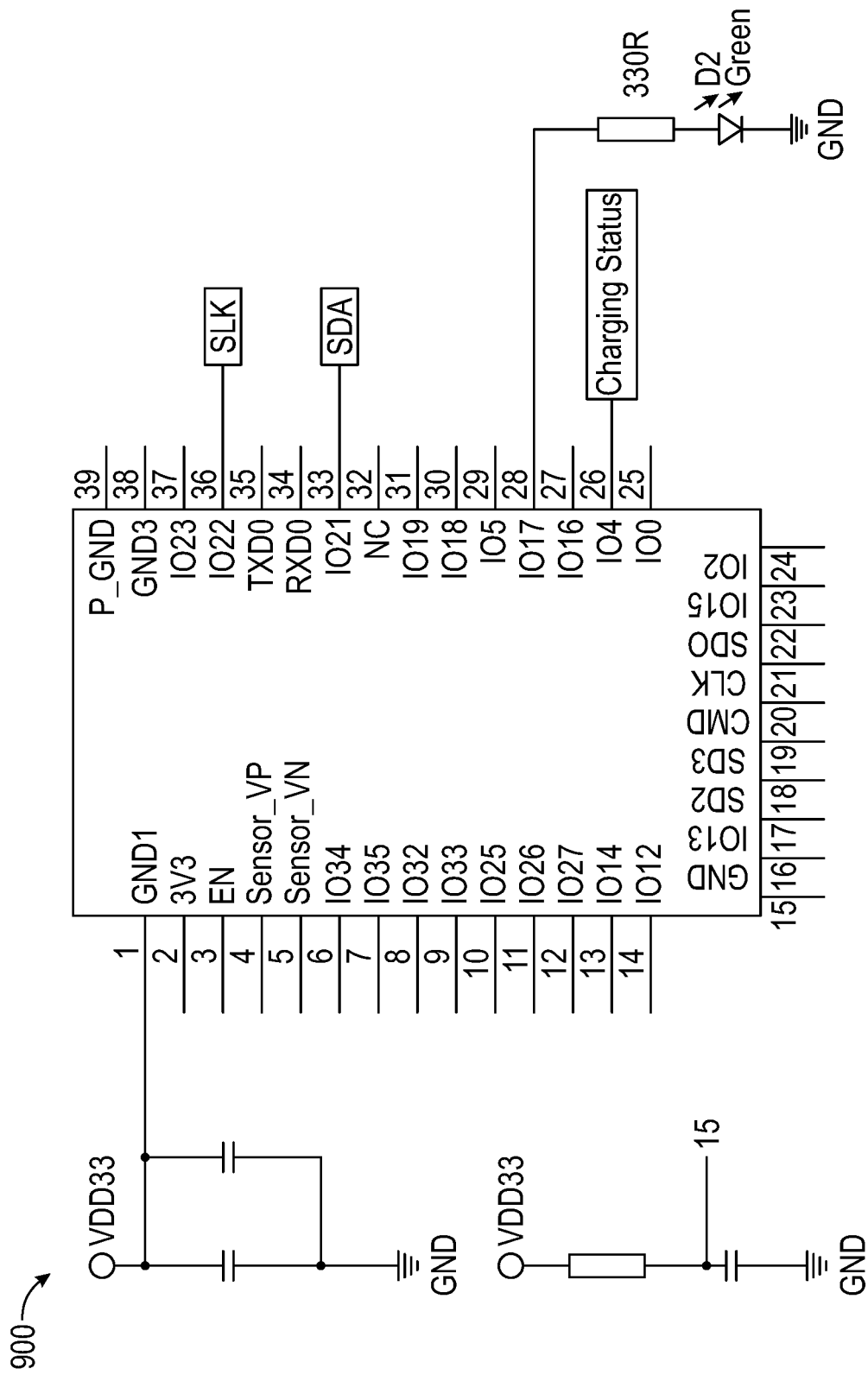
FIG. 9 is a schematic diagram illustrating a combination of circuit components of the present disclosure.

FIG. 9 is a schematic diagram 900 illustrating a combination of circuit components of the present disclosure. The diagram 900 can be configured to h processes GSR analog data (obtained from the leads of the fluidic device 102 of FIG. 1) and converts the data to digital information. Microcontrollers detect binary signals, also known as digital signals. When a microcontroller is powered from five volts (for example), the microcontroller uses zero volt reference (0V) as a binary 0 and five volts (5V) as a binary 1. If the signal is lower than 5V or 2.72V, then the MCU measures this variant analog signal and converts it to a Binary value between 0-255 (256 bits). The 5V analog sensor may output 0.01V or 4.99V or anything in between. The microcontroller has a device built into it that converts the variant GSR sense voltage into values that can be stored in a digital storage medium or relayed over a wireless network (see network 108 of FIG. 1).

Figure 10:
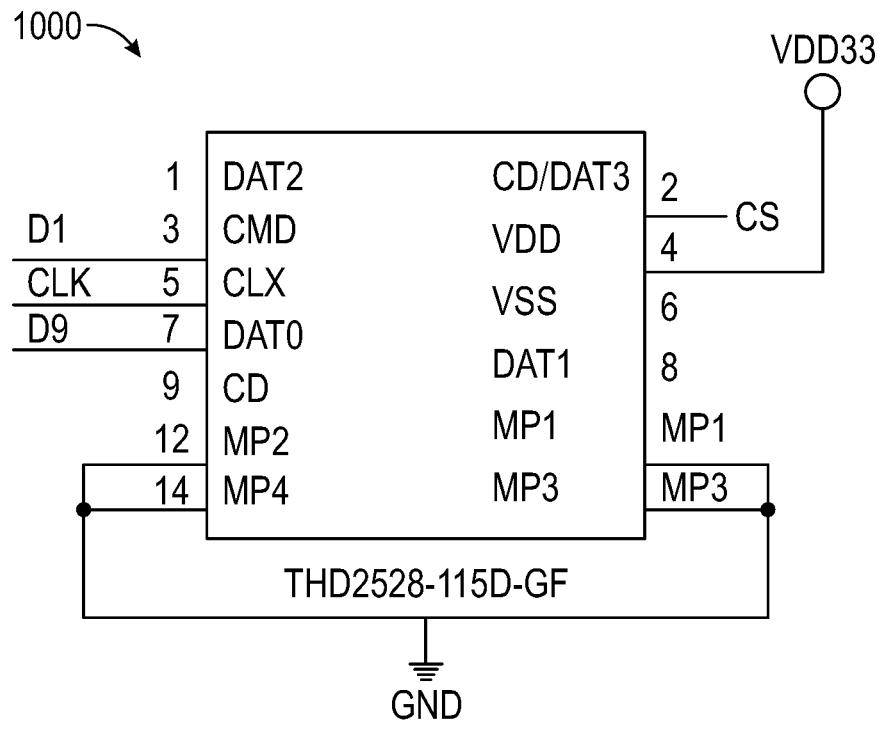
FIG. 10 is a circuit diagram of an example logger memory device.

FIG. 10 is a circuit diagram of an example logger memory device 1000 that can be utilized in the galvanic skin response circuit 200 of FIG. 2. The logger memory device 1000 can log analog data created by an amplifier (see GSR amplifier 800 of FIG. 8) and processed by a processor (see schematic diagram 900 of FIG. 9). In some embodiments, a SD (secure digital) card is also attached with the microcontroller of the GSR amplifier 800 so that it can store data offline. The SD card communicates on SPI interface and may communicatively couple with a clock and data line of SPI module of ESP32 microcontroller of the GSR amplifier 800.

Figure 11:
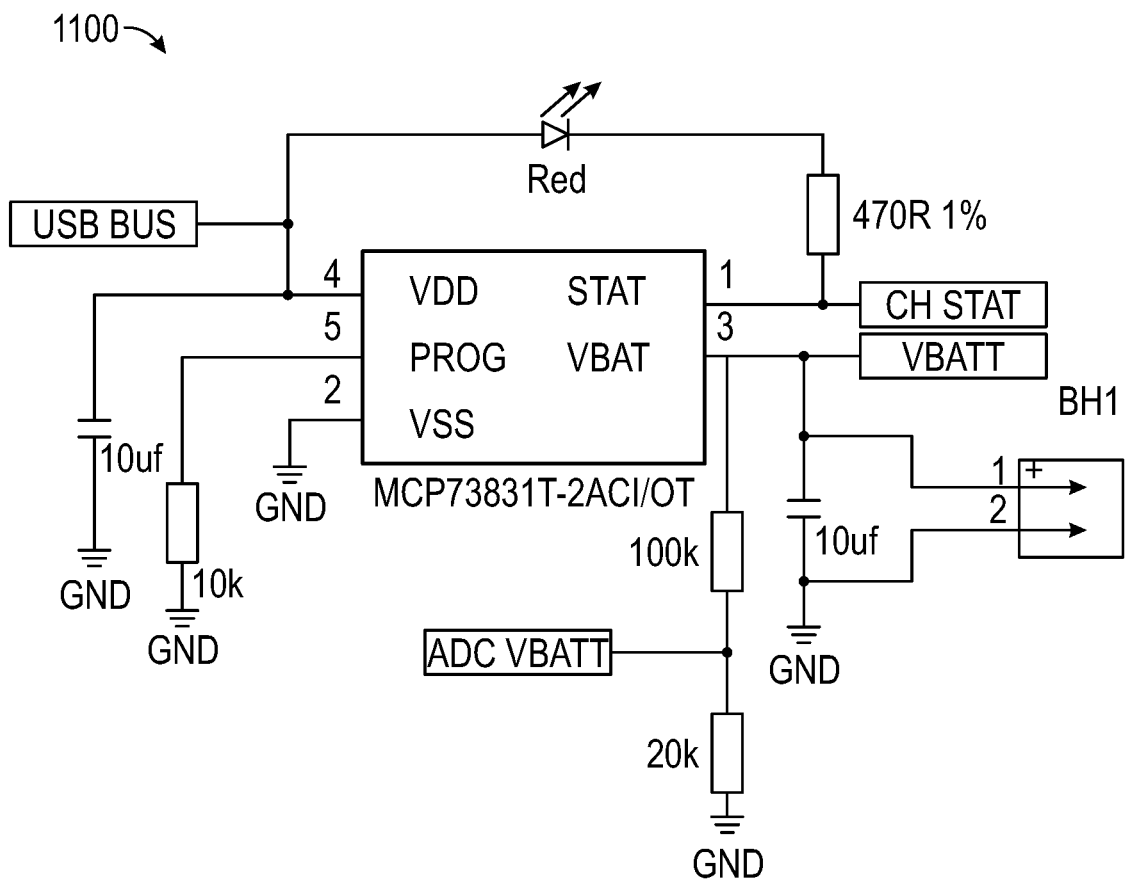
FIG. 11 is a schematic diagram of an example lithium ion battery charging controller.

FIG. 11 is a schematic diagram of an example lithium ion battery charging controller 1100 that can be utilized in the galvanic skin response circuit 200 of FIG. 2. The charging controller 1100 may be powered by a USB connector and also it can obtain power from a battery. A charging IC may be added to charge the battery from USB connector. In some embodiments, a charging IC is utilized when the battery cannot be charged directly by 5V power. The battery may also utilize different current rates at different voltage levels and charging IC manages all these parameters and smoothly charges the battery.

Figure 12:
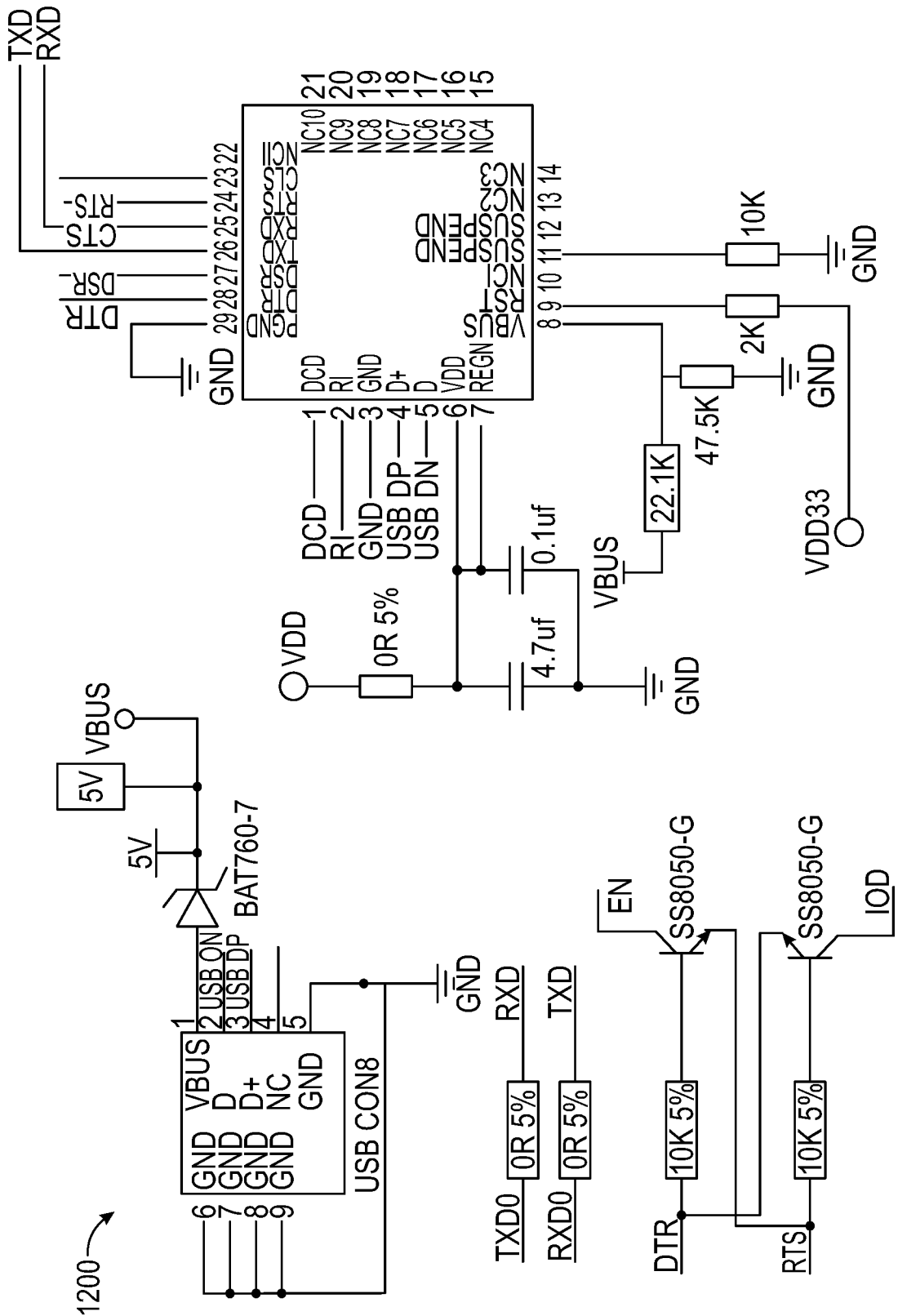
FIG. 12 is a circuit diagram of an example serial COM USB I/O control device.

FIG. 12 is a circuit diagram of an example serial COM USB I/O control device 1200 that can be utilized in the galvanic skin response circuit 200 of FIG. 2. A Universal Serial Bus (USB) to UART converter is added so that ESP microcontroller can communicate with host via USB connector. A 3.3V regulator is added to convert the battery's 4.2V to 3.3V. An RTC circuit may be used to track date and time even when power is off. The RTC IC uses I2C to communicate with ESP32 controller.

Figure 13:
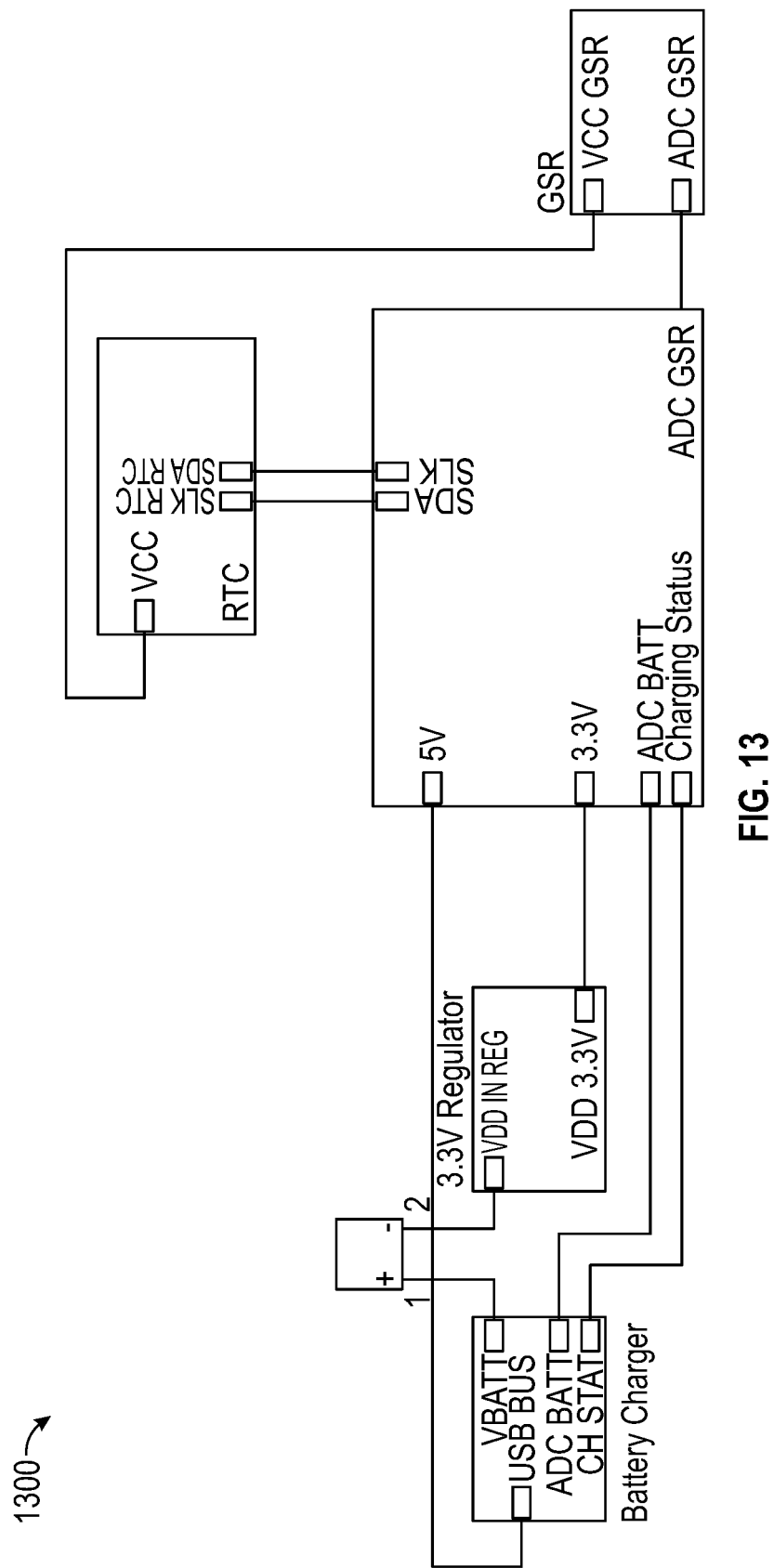
FIG. 13 is a circuit diagram of example serial GSR fluid retention hardware.

FIG. 13 is a circuit diagram of example serial GSR fluid retention hardware 1300. The circuit diagram of FIG. 13 shows example components in the hardware used to gather patient fluid retention information via GSR readings and relay said GSR arbitrated readings to a remote device via BLE (Bluetooth™ as an example). The circuit diagram connects to 5V charger which services a 3.7V LiPo (Lithium Polymer) battery. The GSR fluid retention hardware 1300 further provides a battery power monitor circuit.

Figure 14:
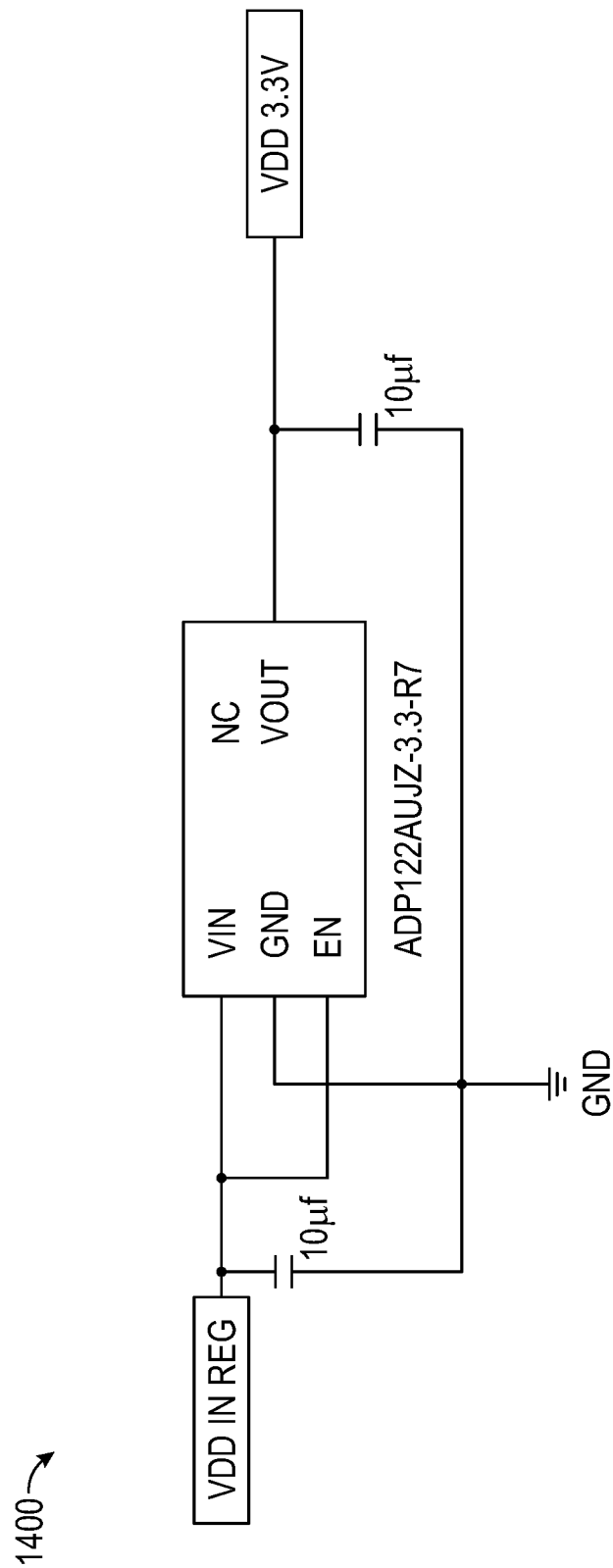
FIG. 14 is a diagram of a voltage regulator.

FIG. 14 is a diagram of a voltage regulator 1400 that can be utilized in the galvanic skin response circuit 200 of FIG.

2. The voltage regulator 1400 may generate a fixed output voltage of a preset magnitude that remains constant regardless of changes to its input voltage or load conditions. This voltage regulator 1400 compares an output voltage with a precise reference voltage and may adjust the pass device (such as a BJT/Bipolar-Junction Transformer) to maintain a constant output voltage to a charger circuit (charging controller 1100 of FIG. 11).

Figure 15:
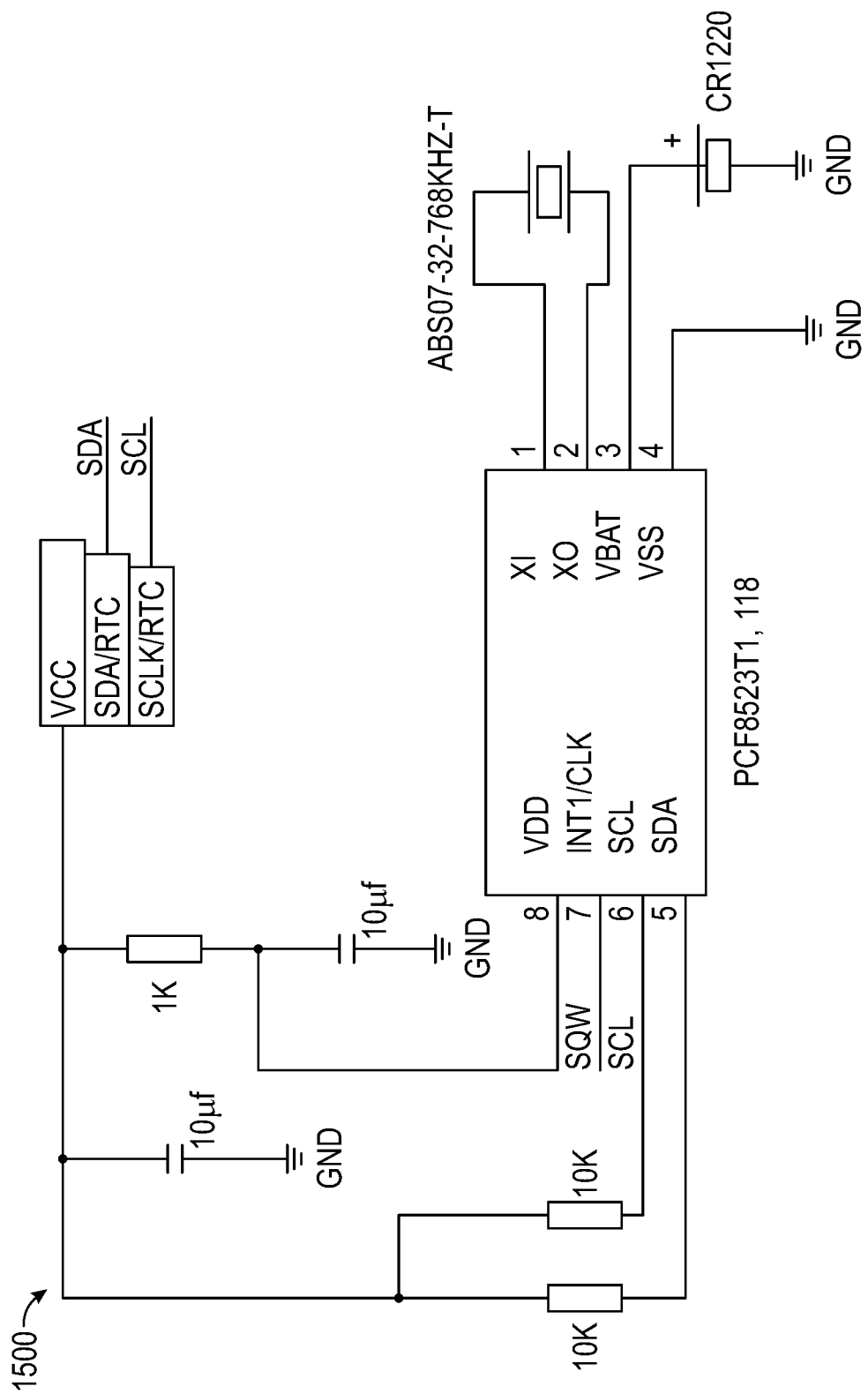
FIG. 15 is a diagram of a synchronous clock circuit.

FIG. 15 is a diagram of a synchronous clock circuit 1500 that can be utilized in the galvanic skin response circuit 200 of FIG. 2. The synchronous clock circuit 1500 maintains time by counting cycles of an oscillator with an external 32.768 kHz crystal oscillator circuit, an internal capacitor based oscillator, or alternatively an embedded quartz crystal. This circuit detects transitions and counts the periodicity of an input that may be connected. The synchronous clock circuit 1500 enables timestamping of GSR values and corresponding fluidic volume measurements. This allows for tracking data changes over time and the generation of graphical representations as disclosed above. The synchronous clock circuit 1500 may use an RTC and a crystal oscillator to intermittently wake up and grab data which is stored in the storage medium as disclosed herein.

In example use cases, patient fluidic volume measurements can be generated or even received and displayed at specific geographical locations by example fluid retention measurement device(s) of the present disclosure. For example, device information can be accessible to a remote physician while in a hospital for in-room telemetry readings for health care providers, while the patient is in a clinic visiting attending physician who has been remotely viewing the patient's fluid retention levels and while the patient is at home. The health care provider or tending physician can monitor fluid levels of the patient.

When data related to fluidic volume measurements are provided to a physician. When the fluidic volume measurements are indicative of an increase in fluid volume in the patient, the physician can remedy these volumetric changes by prescribing a diuretic. In some embodiments, the galvanic skin response circuit 200 of FIG. 2 can be programmed to calculate a specified dosage of the diuretic using the fluidic volumetric changes of the patient, along with pertinent biometric parameters of the patient. In some instances, the volumetric changes galvanic skin response circuit 200 can be programmed to store pertinent biometric parameters for the patient that can be transmitted to a service provider such as a physician or hospital system. To be sure, this can include transmitting the pertinent biometric parameters and/or the fluidic volumetric changes to a computer in the physician's office or a hospital computing system.

In some instances, the galvanic skin response circuit 200 can sense and transmit only GSR data that are indicative of changes in GSR of the patient over time. A receiver such as a physician or hospital system can convert the GSR data to fluidic volumetric values.

While the above disclosure references a compression stocking for measuring fluidic volume changes in a patient, and specifically changes in water volume of the patient, the present disclosure is not so limited to only compression stockings for measuring changes in water volume. In some embodiments, aspects of the present disclosure can be used to determine fluidic volumetric values and changes over time for other body parts such as breast tissue. An example device, such as a brazier, can be constructed to include a fluid monitoring device. Rather than incorporating leads and a control unit to compression stocking, the leads and control unit can be integrated into a brazier. For example, a pair of leads can be integrated into a material that forms a cup of a brazier. Terminal ends of the leads can be located inside the cup to allow for contact between the leads and the skin of the breast of an individual. The control unit can be identical in construction to the control unit of FIG. 1.

In operation, the brazier augmented with a fluid monitoring device can be used to determine changes in fluidic volume due to events such as breastfeeding. Thus, using the brazier augmented with a fluid monitoring device, a user can determine how much breast milk has been consumed by a nursing child.

In some embodiments, the user or a medical professional can determine a child's weight in ounces. The weight can be divided by 6: 132 oz/6=22 oz). This value presents how many ounces of breast milk the child should be getting in one day. Based on the weight above, the child should be taking in about 22 ounces of breast milk in a 24 hour period. Thus assessing the amount of breast milk produced, retained and consumed within 24 hours via the mother becomes of great importance.

A brazier augmented with a fluid monitoring device can employ galvanic skin response to plot changes in volumetric fluid changes in a breast when compared to baseline breast volume thus allowing retrospective analysis of breast milk consumed, retained, and produced. Changes in breast fluidic volume can be analyzed over time and quantified to allow a nursing mother to know how may ounces of milk have been produced, consumed, and/or retained.

Figure 16:
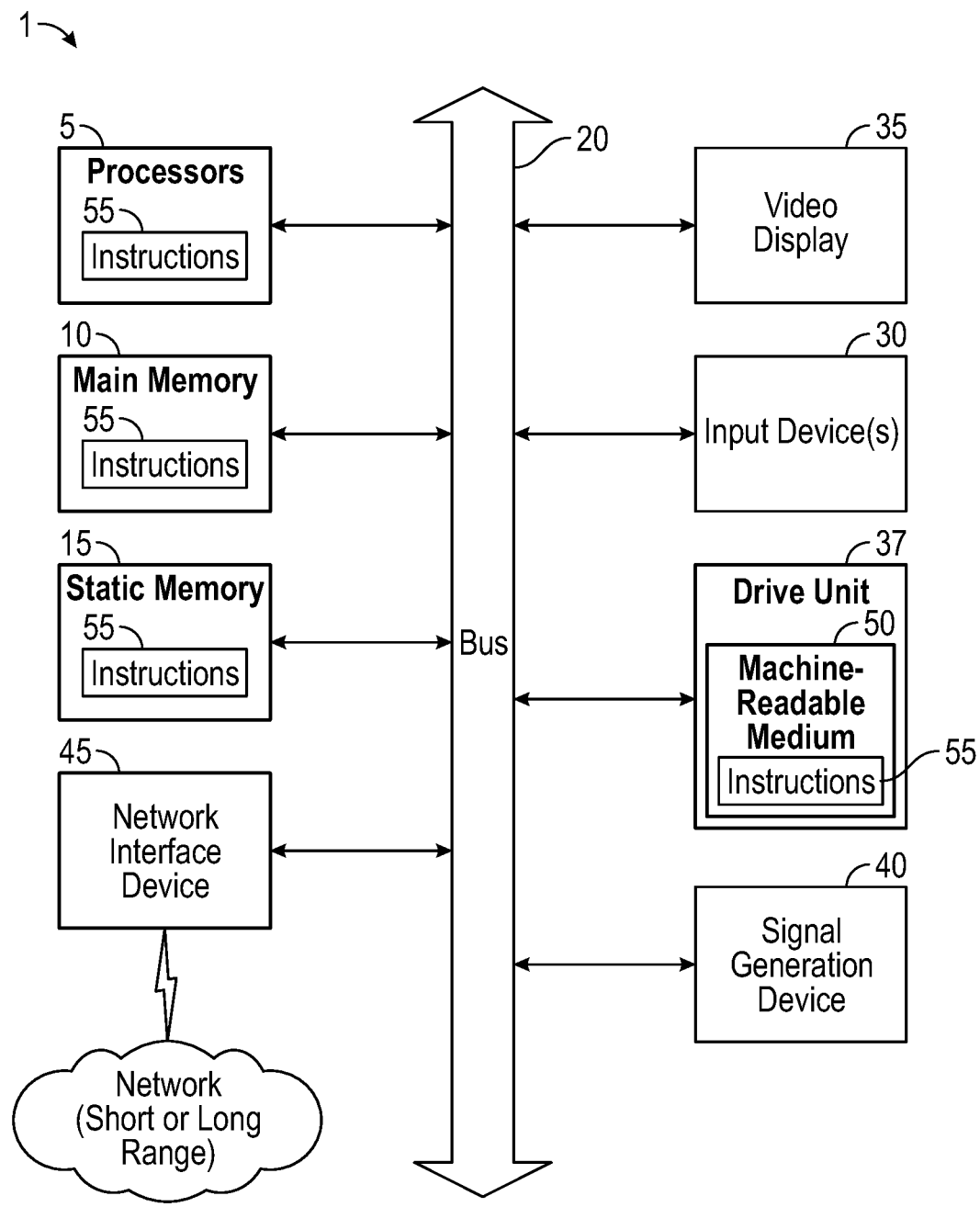
FIG. 16 is a schematic diagram of an example computer system that can be used to practice aspects of the present disclosure.

FIG. 16 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as a Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alphanumeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

In this description, for purposes of explanation and not limitation, specific details are set forth, such as particular embodiments, procedures, techniques, etc. in order to provide a thorough understanding of the present invention.

However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

That which is claimed is:

1. A device for measuring fluid retention in a patient, the device comprising:
   a compression stocking;
   a first lead integrated into the compression stocking;
   a second lead integrated into the compression stocking, wherein a terminal end of the first lead and a terminal end of the second lead are spaced apart from one another, each of the terminal ends being capable of contacting skin of a foot of a patient; and
   a control unit configured to electrically couple with the first lead and the second lead, the control unit comprising a microcontroller configured to measure galvanic skin response values of the patient over time, the galvanic skin response values being indicative of a fluidic retention of the patient.

2. The device according to claim 1, wherein the microcontroller is configured to convert the galvanic skin response values to fluidic volume values.

3. The device according to claim 1, wherein the first lead comprises a first conductive interface disposed at a top of the compression stocking and the second lead comprises a second conductive interface disposed at the top of the compression stocking.

4. The device according to claim 3, wherein control unit comprises a first conductor pin and a second conductor pin, the first conductor pin being configured to snap into the first conductive interface, the second conductor pin being configured to snap into the second conductive interface, the first conductor pin and the second conductor pin being electrically coupled to the microcontroller.

5. The device according to claim 1, wherein the galvanic skin response values are obtained according to a user-defined interval.

6. The device according to claim 1, wherein the microcontroller is configured to convert the galvanic skin response values to fluidic volume values, wherein the control unit comprises a communications module that allows for transmission of the galvanic skin response values or the fluidic volume values to a service provider over a network.

7. The device according to claim 1, wherein the microcontroller is configured to store a fluid volume threshold, further wherein when the galvanic skin response values that are indicative of the fluidic retention of the patient meets or exceeds the fluid volume threshold, the microcontroller transmits an alert message to over the network to a service provider.

8. The device according to claim 1, wherein the first lead functions as an anode and the second lead functions as a cathode.

9. A device for measuring fluid retention in a patient, the device comprising:
   a garment that is worn on a patient, the garment comprising a anode lead and a cathode lead woven into the garment; and
   a control unit configured to electrically couple with the anode lead and the cathode lead, the control unit being configured to:
   emit transmitted electrical signals through the anode lead;
   measure received electrical signals from the cathode lead;
   calculate galvanic skin response based on the transmitted electrical signals and the received electrical signals; and
   convert the galvanic skin response to fluid volume.

10. The device according to claim 9, wherein the control unit collects the galvanic skin response over a period of time to determine changes in the fluid volume over the period of time.

11. The device according to claim 9, wherein the control unit is configured to transmit an alert to a physician when the fluid volume exceeds a fluid volume threshold or trigger.

12. The device according to claim 9, wherein the anode lead comprises a first conductive interface and the cathode lead comprises a second conductive interface.

13. The device according to claim 12, wherein the control unit comprises a housing that encloses a microcontroller, a resistive-capacitive time circuit, and a communications interface.

14. The device according to claim 13, wherein the housing comprises a first conductor pin and a second conductor pin, the first conductor pin being configured to snap into the first conductive interface, the second conductor pin being configured to snap into the second conductive interface, the first conductor pin and the second conductor pin being electrically coupled to the microcontroller.

15. The device according to claim 9, wherein the galvanic skin response values are obtained according to a user-defined interval.

16. A method for measuring fluid retention in a patient, the method comprising:
   providing a compression stocking to a patient, the compression stocking comprising a first lead integrated into the compression stocking and a second lead integrated into the compression stocking, the compression stocking configured to couple with a control unit that is configured to generate galvanic skin response data or fluid volume data; and transmitting the galvanic skin response data or the fluid volume data from the control unit to a service provider.

17. The method according to claim 16, further comprising generating a graphical display of the galvanic skin response data or the fluid volume data.

18. The method according to claim 16, further comprising obtaining a baseline fluid volume for the patient.

19. The method according to claim 18, further comprising:

determining when the fluid volume data meet or exceed a threshold compared with the baseline fluid volume; and transmitting an alert to a physician when the fluid volume data meet or exceed the threshold.

20. The method according to claim 16, further comprising converting, by the service provider, the galvanic skin response data into the fluid volume data.

* * * * *